(12) United States Patent
Chabrier de Lassauniere et al.

(10) Patent No.: US 7,244,711 B2
(45) Date of Patent: Jul. 17, 2007

(54) ASSOCIATION OF CALPAIN INHIBITORS AND REACTIVE OXYGEN SPECIES TRAPPING AGENTS

(75) Inventors: Pierre-Etienne Chabrier de Lassauniere, Paris (FR); Bernadette Pignol, Paris (FR); Serge Auvin, Mauchamps (FR)

(73) Assignee: Societe de Conseils de Recherches et d' 'Applications Scientifiques S.C.R.A.S (FR)

( * ) Notice: Subject to any disclaimer, the term of this patent is extended or adjusted under 35 U.S.C. 154(b) by 0 days.

(21) Appl. No.: 10/415,638

(22) PCT Filed: Nov. 14, 2001

(86) PCT No.: PCT/FR01/03558

§ 371 (c)(1),
(2), (4) Date: Apr. 30, 2003

(87) PCT Pub. No.: WO02/40016

PCT Pub. Date: May 23, 2002

(65) Prior Publication Data

US 2004/0053851 A1    Mar. 18, 2004

(30) Foreign Application Priority Data

Nov. 15, 2000  (FR)  .................................. 00 14690

(51) Int. Cl.
*A61K 38/05* (2006.01)
*A61K 31/33* (2006.01)
*C07K 5/06* (2006.01)

(52) U.S. Cl. ........................................ 514/19; 514/183
(58) Field of Classification Search ................... 514/2, 514/18, 19
See application file for complete search history.

(56) References Cited

U.S. PATENT DOCUMENTS 5,760,048 A    6/1998   Wang et al.

FOREIGN PATENT DOCUMENTS

JP    2000191616   11/2000

WO    0132654   5/2001

OTHER PUBLICATIONS

AM Mortensen and RF Novak. Toxicol. Appl. Pharmacol. (1992) 117, 180-188.*
"Inhibitor" Merriam-Webster Online Dictionary. Accessed Dec. 6, 2004 http://www.m-w.com/cgi-bin/dictionary.*
Definition of Cancer. Internet document <<http://www.medterms.com>> 1 page, accessed Sep. 16, 2005, last reviewed Sep. 18, 2004.*
Cachexia. Internet document <<http://www.phytomedical.com/cachexia/cachexia.asp>> 3 pages, accessed Jul. 24, 2006.*
Hearing Loss and Deafness: Merck Manual Home Edition. Internet document <<http://www.merck.com/mmhe/print/sec19/ch218/ch218a.html>>, 7 pages, accessed Jul. 24, 2006, reviewed Feb. 1, 2003.*
Kim et al, "Regulation . . . Fibroblasts", Cellular Signalling, (2002) 14/3 (205-210).
Banik et al, "Role . . . Inhibitors", Annals New York Academy of Sciences, (1998), 844 (Neurochemistry of Drugs of Abuse), 131-137, XP008000950.
Blumenthanl et al, "Changes . . . Hydroxytoluene", Archives of Biochemistry and Biophysics, New York, vol. 256, No. 1, Jul. 1987 pp. 19-28.
Wang et al, "An . . . NEUROPROTECTIVE", Proceedings of the National Academy of Science, Washington, US, vol. 93, No. 13, Jun. 25, 1996, pp. 6687-6692.
Perrin et al, "Mise . . . Recovery", Archives Des Maladies Du Coeur et des Vaisseaux, J.B. Balliere, Paris, France, vol. 93, No. 8, Aug. 2000, pp. 931-936.
Guttmann et al, "Oxidative . . . in Situ", Journal of Biological Chemistry, American Society of Biological Chemists, Baltimore, MD, US, vol. 273, No. 21, May 22, 1998, pp. 13331-13338.

* cited by examiner

*Primary Examiner*—Cecilia Tsang
*Assistant Examiner*—Andrew D. Kosar
(74) *Attorney, Agent, or Firm*—Charles A. Muserlian

(57) ABSTRACT

The invention concerns a pharmaceutical composition comprising, as active principle, at least a calpain inhibiting substance and at least a substance trapping reactive oxygen species (ROS), and optionally an acceptable pharmaceutical carrier. The invention also concerns a product comprising at least a calpain inhibiting substance and at least a substance trapping reactive oxygen species (ROS), selectively or not, as combination product, the active principle being separate.

1 Claim, No Drawings

ASSOCIATION OF CALPAIN INHIBITORS AND REACTIVE OXYGEN SPECIES TRAPPING AGENTS

This application is a 371 of PCT/FR01/03558 filed Nov. 14, 2001.

The present invention relates to a pharmaceutical composition comprising, as active ingredient, at least one substance which inhibits calpains and at least one substance which traps the reactive oxygen species (ROS), and optionally a pharmaceutically acceptable support. The invention also relates to a product comprising at least one substance which inhibits calpains and at least one substance which traps reactive oxygen species, selectively or non-selectively, as a combination product, in separated form, of these active ingredients.

BACKGROUND OF THE INVENTION

Given the potential role of calpains and of ROS's in physiopathology, a composition according to the invention can produce beneficial or favourable effects in the treatment of pathologies where these enzymes and/or these radicular species are involved, and in particular:
- inflammatory and immunological diseases such as for example rheumatoid arthritis, pancreatitis, multiple sclerosis, inflammations of the gastro-intestinal system (ulcerative or non-ulcerative colitis, Crohn's disease),
- cardiovascular and cerebrovascular diseases including for example arterial hypertension, septic shock, cardiac or cerebral infarctions of ischemic or hemorragic origin, ischemias as well as disorders linked to platelet aggregation,
- disorders of the central or peripheral nervous system such as for example neurodegenerative diseases where there can in particular be mentioned cerebral or spinal cord trauma, sub-arachnoid hemorrage, epilepsy, ageing, senile dementia including Alzheimer's disease, Huntington's chorea, Parkinson's disease, peripheral neuropathies,
- osteoporosis,
- muscular dystrophies, cachexia,
- proliferative diseases such as for example atherosclerosis or recurrence of stenosis,
- loss of hearing
- cataracts,
- organ transplants,
- auto-immune and viral diseases such as for example lupus, AIDS, parasitic and viral infections, diabetes and its complications, multiple sclerosis,
- cancer,
- all pathologies characterized by an excessive production of ROS's and or activation of calpains.

In all these pathologies, there is experimental evidence demonstrating the involvement or ROS's (Free Radic. Biol. Med. (1996) 20, 675–705; Antioxid. Health. Dis. (1997) 4 (Handbook of Synthetic Antioxidants), 1–52) as well as the involvement of calpains (Trends Pharmacol. Sci. (1994) 15, 412419; Drug News Perspect (1999) 12, 73–82). As an example, cerebral lesions associated with cerebral infarctions or with experimental cranial traumatism are reduced by antioxidant agents (Acta. Physiol. Scand. (1994) 152, 349–350; J. Cereb. Blood Flow Metabol. (1995) 15, 948–952; J Pharmnacol Exp Ther (1997) 2, 895–904) as well as by calpain inhibitors (Proc Natl Acad Sci USA (1996) 93, 3428–33; Stroke, (1998) 29, 152–158; Stroke (1994) 25, 2265–2270). No combination with a therapeutic aim of these two active ingredients, namely a substance inhibiting calpains and a substance which traps reactive oxygen species, has been described in the literature. Moreover, these two active ingredients act synergistically.

OBJECTS OF THE INVENTION

A subject of the present invention is therefore a pharmaceutical composition comprising, as active ingredient, at least one substance which inhibits calpains and at least one substance which traps reactive oxygen species, and optionally a pharmaceutically acceptable support. In the present application, the expression "at least one substance which inhibits calpains and at least one substance which traps reactive oxygen species" signifies the combination of at least two different entities, one a calpain inhibitor and the other free radical traps.

A more particular subject of the invention is a pharmaceutical composition comprising, as active ingredient, a substance which inhibits calpains and a substance which traps reactive oxygen species, and optionally a pharmaceutically acceptable support.

BRIEF DESCRIPTION OF THE INVENTION

By the term reactive oxygen species trap, it should be understood any chemical or enzymatic substance capable of opposing or of trapping the or one of the reactive oxygen species such as $O_2^-$, OH, $RO_2^+$, $RO^+$, $ONO_2^-$, $NO^+$, $NO_2^+$ or $H_2O_2$ (Halliwell B., Gutteridge JMC., Free radicals in biology and medicine, $2^{nd}$ ed., Oxford, Clarendon Press, 1989). These substances can be natural or synthetic and have antioxidant properties. (Santrucek and Krepelka, Antioxidants—Potential chemotherapeutic agents Drugs Future 13, 975–996, 1988; Jackson et al, Antioxidants: a biological defense mechanism for the prevention of atherosclerosis, Med. Res. Reviews 13, 161–182 (1993); Aruoma, Characterization of drugs as antioxidant prophylactics, Free Rad. Biol. Med. 20, 675–705 (1996)). The antioxidant activity of a chemical substance can be determined by standard pharmaceutical tests such as those illustrated in the experimental part of the present Application. Such an antioxidant substance can thus display, on lipidic peroxidation (cf test in the experimental part), an $IC_{50}$ of less than 100 μM and preferably less than 10 μM.

Calpains are proteolytic cytosolic enzymes which belong to the protease cysteine family. Activation of calpains is strictly dependent on calcium (Suzuki et al. Calpain: Novel family members, activation, and physiological function (1995) Biol. Chem, Hoppe-Seyler, 376, 523–529). Under normal physiological conditions, these enzymes are not activated or slightly activated. On the contrary, the excessive rise in intracellular calcium which is observed in certain physiopathological phenomena induces strong activation of the calpains. This activation leads to selective cleavage and consequently to the loss of function of cytoskeletal proteins, membrane receptor or transcription factors leading to cell death and tissue degradation. Activation of the calpains appears to play a major and deleterious role in several pathologies such as for example neurodegenerative diseases, cerebral ischemia or muscular dystrophies, which could optionally correct inhibitors of these enzymes (Wank K et al. Calpain inhibition: an overview of its therapeutical potential (1994) Trends in Pharmacological Sciences 15, 412–419). The inhibitory activity of a chemical substance vis à vis the calpains can be determined by standard pharmaceutical tests such as those illustrated in the experimental part of the present Application. Such a substance which inhibits calpains can thus have, as regards the inhibition of calpain (cf test in the experimental part of the present Application), an $IC_{50}$ less than 10 μM.

DETAILED DESCRIPTION OF THE INVENTION

A subject of the invention is also a product comprising at least one substance which inhibits calpains and at least one substance which traps reactive oxygen species as a combination product, in separated form, for simultaneous or sequential use in the treatment of pathologies in which calpains and reactive oxygen species are involved, pathologies such as inflammatory and immunological diseases, cardiovascular and cerebrovascular diseases, disorders of the central nervous system, osteoporosis, muscular dystrophies, cachexia, loss of hearing, proliferative diseases, cataracts, organ transplants, auto-immune and viral diseases, cancer and all pathologies characterized by excessive production of ROS's and/or activation of calpains, and preferably, disorders of the central or peripheral nervous system, muscular dystrophies, cachexia, loss of hearing and cataracts.

In a pharmaceutical composition or a product according to the invention, the calpain inhibitor and the reactive oxygen species trap can be presented in doses which can be identical or different. Dosages are chosen as a function of the compounds combined with appropriate diluents or excipients.

The calpain inhibitor and the reactive oxygen species trap can be administered simultaneously or sequentially, by the same administration route or by different routes. Preferably, the administration routes are oral, parenteral or topical.

The reactive oxygen species traps can be chosen for example from ascorbic acid, ethoxyquin, N-acetyl-cysteine, carotene derivatives namely α-, β-, γ- or δ-carotene and more particularly β-carotene (Hao Chen et al, Free Radical Biology and Medicine 18 (5), 949–953 (1995)), 2,2,5,5-tetramethyl-3-pyrroline-1-oxyl-3-carboxylic acid, ubiquinones such as the Q10 coenzyme (S. Tereao et al., J. Org. Chem., 44, 868 (1979)) or captodative compounds (H. G. Viehe et al., Acc. Res., 18, 148–154 (1985), incorporated by way of reference in the present Application). The reactive oxygen species traps can also be chosen for example from nitrones, phenolic compounds, indole derivatives, indolines, imidazoles, phenothiazines, phenoxazines, phenazines, diphenylamines or carbazoles, or also from enzymes capable of neutralizing the or one of the reactive oxygen species such as superoxide dismutases, catalases or glutathion peroxidases and their mimetics.

As examples of reactive oxygen species trap nitrones, there can be mentioned the compounds as defined in Patent Applications WO 96/15110, WO 88/05044 and U.S. Pat. No. 5,310,916 (incorporated in the present Application by way of reference) but also tempol and N-tert-butyl-α-phenyl-nitrone.

Among the examples of phenolic compounds which trap reactive oxygen species, there can be mentioned probucol, NDGA, tocopherol derivatives namely α-, β-, γ-, ε-, τ- or δ-tocopherol, or phenolic flavonoids (R. A. et al, Phytochemistry, 27(4), 969–978 (1988), incorporated in the present Application by way of reference). The phenolic compounds which trap reactive oxygen species can also be chosen from the compounds of general formula $I_A$ or $II_A$

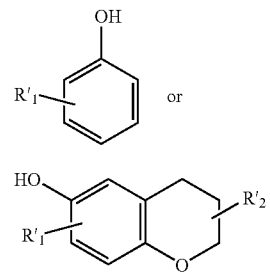

in which $R'_1$ represents one or more substituents chosen from the hydrogen atom, the hydroxy, halo, carboxy, lower alkyl, lower alkoxy, lower alkenyl or alkoxycarbonyl radicals, the alkyl, alkoxy and alkenyl radicals being optionally substituted by a hydroxy, halo, carboxy or amino radical; and $R'_2$ represents one or more substituents chosen from the hydrogen atom or the optionally substituted lower alkyl, lower alkoxy, hydroxy, halo, amino or carboxy radicals. Preferably, the compounds of general formula $I_A$ or $II_A$ are 3-5-di-tert-butyl-4-hydroxybenzoic acid, 2,3,6-trimethyl-2-hexyloxy-phenol, 2,6-di-tert-butyl-4-methoxy-phenol, 2,6-di-tert-butyl4-methyl-phenol, trolox, n-propyl gallate, eugenol, cafeic acid, sinapinic acid, gallic acid and propofol.

The reactive oxygen species trapping indole derivatives can be compounds as defined in Application No. WO 96/26941. They can also be compounds of general formula $III_A$

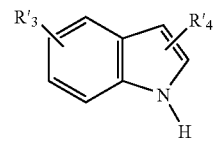

in which $R'_3$ represents one or more substituents chosen from the hydrogen atom, the hydroxy, halo, lower alkyl or lower alkoxy radicals; $R'_4$ represents one or more substituents chosen from the hydrogen atom, the halo, hydroxy, amino, carboxy or alkylcarbonylaminoalkyl radicals. Preferably, the compounds of formula $III_A$ are melatonin, 5-hydroxy-tryptamine, 5-hydroxy-indole-2-carboxylic acid.

Among the reactive oxygen species trapping indoline derivatives, there can be mentioned-5-amino-indoline and N-alkyl-indolines and more particularly N-methyl-indoline.

Among the reactive oxygen species trapping imidazoles, there can be mentioned imidazole itself or cimetidine.

Among the reactive oxygen species inhibitors there can also be mentioned the compounds of formula $IV_A$ or $V_A$

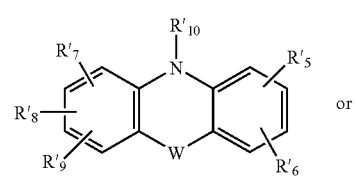

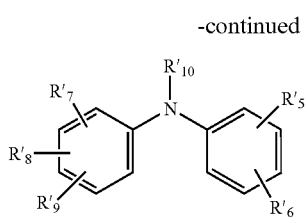

in which R'₅, R'₆, R'₇, R'₈, R'₉ represent, independently, a hydrogen atom, an alkyl, alkoxy cyano, halo, hydroxy, nitro or —NR'₁₁R'₁₂ radical, R'₁₁ and R'₁₂ represent, independently, a hydrogen atom, an alkyl radical or a —COR'₁₃ group or R'₁₁ and R'₁₂ form together with the nitrogen atom to which they are attached an optionally substituted heterocycle, R'₁₃ represents a hydrogen atom, an alkyl, alkoxy or —NR'₁₄R'₁₅ radical, R'₁₄ and R'₁₅ represent, independently, a hydrogen atom or an alkyl radical, or R'₁₄ and R'₁₅ form together with the nitrogen atom to which they are attached an optionally substituted heterocycle, R'₁₀ represents a hydrogen atom, an alkyl radical or a —COR'₁₆ group, R'₁₆ represents a hydrogen atom, an alkyl, alkoxy or —NR'₁₇R'₁₈ radical, R'₁₇ and R'₁₈ represent; independently, a hydrogen atom or an alkyl radical, or R'₁₇ and R'₁₈ form together with the nitrogen atom to which they are attached an optionally substituted heterocycle, W represents a bond, O or S or also an —N(R'₁₉)— radical, in which R'₁₉ represents a hydrogen atom or an alkyl radical.

As examples of carbazoles, there can be mentioned carvedilol or the compounds of formula IV_A, and more particularly 4-hydroxycarbazole. As other examples of compounds of formula IV_A, there can also be mentioned phenothiazines and more particularly 2-methoxyphenothiazine, phenoxazines and phenazines. As examples of compounds of formula V_A, there can be mentioned diphenylamines such as 4-hydroxydiphenylamine 4-aminodiphenylamine or 4-methoxy-N-(4-methoxyphenyl)aniline.

A more particular subject of the invention is a composition or product as defined above, in which the calpain inhibitor is 3-(4-iodophenyl)-2-mercapto-2-propenoic acid (PD150606).

A more particular subject of the invention is a composition or product as defined above, in which the calpain inhibitor corresponds to formula I_B

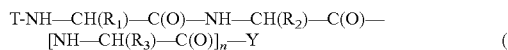

in which

R₁, R₂ and R₃ represent, independently, the hydrogen atom or a lower alkyl radical optionally substituted by one or more substituents chosen from: hydroxy, lower alkoxy, mercapto, lower alkylthio, carboxy, aminocarbonyl, (lower alkyl)aminocarbonyl, di(lower alkyl)aminocarbonyl, amino, guanidino, optionally substituted aryl or optionally substituted heteroaryl, the substituent(s) of the aryl and heteroaryl radicals being chosen from: halo, hydroxy, lower alkyl or lower alkoxy;

Y represents the hydrogen atom or a —C(O)-Ry or —C(O)—O—R'y radical in which
  Ry represents a lower alkyl or —N(Ry₁)(Ry₂) radical;
  R'y represents the hydrogen atom or a lower alkyl or lower arylalkyl radical;
  Ry₁ and Ry₂ represent, independently, the hydrogen atom, a lower alkyl, lower alkoxy, lower arylalkyl, lower heteroarylalkyl, cycloalkyl-alkyl, heterocycloalkyl radical, these radicals being able to be substituted by one or more identical or different substituents chosen from: halo, hydroxy, trifluoromethyl, lower alkyl, lower alkoxy, amino, (lower alkyl)amino, di(lower alkyl)amino, aryloxy, arylalkoxy;

n represents 0 or 1;

T represents a radical of formula —C(O)—O-Rt₁ or —C(O)-Rt₂ in which
  Rt₁ represents a lower alkyl or lower arylalkyl radical;
  Rt₂ represents a lower alkyl, lower arylalkyl, aryloxy lower alkyl or a heteroaryl radical.

In the definitions indicated above, the expression halo represents the fluoro, chloro, bromo or iodo radical, preferably chloro, fluoro or bromo. By alkyl, unless otherwise specified, or lower alkyl, is meant a linear or branched alkyl radical containing 1 to 6 carbon atoms such as, for example, the methyl, ethyl, propyl, isopropyl, butyl, isobutyl, sec-butyl and tert-butyl, pentyl, neopentyl, isopentyl, hexyl, isohexyl radicals. The alkoxy radicals, unless otherwise specified, or lower alkoxy can correspond to the alkyl radicals indicated above such as for example the methoxy, ethoxy, propyloxy or isopropyloxy radicals but also linear, secondary or tertiary butoxy. The term lower alkylthio preferably designates the radicals in which the alkyl radical is as defined above such as for example methylthio, ethylthio.

By alkenyl, unless otherwise specified, or lower alkenyl, is meant a linear or branched alkyl radical containing 2 to 6 carbon atoms and having at least one unsaturation (one or more double bond). For example, there can be mentioned the vinyl, allyl, propenyl, isopropenyl, pentenyl, butenyl, hexanyl, propenyl and butadienyl groups. The term cycloalkyl preferably designates the cyclopropyl, cyclobutyl, cyclopentyl or cyclohexyl rings.

The expression aryl represents an aromatic radical, constituted by a condensed ring or rings, such as for example the phenyl or naphthyl radical. The term aryloxy preferably designates the radicals in which the aryl radical is as defined above such as for example the phenoxy radical. The expression heteroaryl designates an aromatic radical, constituted by a condensed ring or rings, with at least one ring containing one or more identical or different heteroatoms chosen from sulphur, nitrogen or oxygen. As an example of a heteroaryl radical, there can be mentioned the thienyl, furyl, pyrrolyl, imidazolyl, pyrazolyl, isothiazolyl, thiazolyl, isoxazolyl, oxazolyl, pyridyl, pyrazinyl, pyrimidyl, quinolinyl, benzothienyl, benzofuryl and indolyl radicals.

The term heterocycloalkyl preferably represents a saturated mono or bicyclic heterocycle, comprising 1 to 5 heteroatoms chosen from O, S, N. For example, there can be mentioned: tetrahydrofuran, tetrahydropyran, oxetane, tetrahydrothiophene, tetrahydrothiopyran, thietane, pyrrolidine, piperidine, azetidine, 1,3-dioxane, 1,3-dioxolane, 1,3-dithiolane, 1,3-dithiane, 1,3-oxathiolane, 1,3-oxazolidine, 1,3-imidazolidine or 1,3-thiazolidine.

The term arylalkyl (or aralkyl) designates a radical in which the aryl and alkyl radicals respectively are as defined above such as for example benzyl, phenethyl or naphthyl-methyl. The alkoxycarbonyl, (alkyl)aminocarbonyl and (dialkyl)aminocarbonyl radicals designate the radicals in which the alkyl and alkoxy radicals respectively have the meanings indicated previously. The terms alkylcarbonylaminoalkyl, aryloxy alkyl, aryl alkoxy, heteroaryl alkyl, cycloalkyl alkyl designate the radicals in which the alkyl, aryloxy, aryl, heteroaryl and cycloalkyl radicals are as defined above.

In the case of the radicals of formula —NR$^i$R$^i$ where R$^i$ and R$^j$ form together with the nitrogen atom to which they are attached an optionally substituted heterocycle, the heterocycle is preferably saturated and comprises 4 to 7 members and 1 to 3 heteroatoms including the nitrogen atom already present, the additional heteroatoms being chosen independently from the group constituted by the O, N and S atoms. Said heterocycle can be, for example, the azetidine, pyrrolidine, piperidine, piperazine, morpholine or thiomorpholine ring. Said heterocycle can be substituted by one or more identical or different substituents chosen from an alkyl, alkoxy, aryl, aralkyl, hydroxy or halo radical.

According to the definition of the variable groups, a compound of formula $I_B$ as defined above, can have one or more asymmetrical carbons. The invention relates to the compounds of formula $I_B$ as defined above, compounds which can be found in racemic, enantiomeric or diastereoisomeric form.

Preferentially, a subject of the invention is a composition or product as defined above, characterized in that the calpain inhibitor corresponds to formula ($I_B$)

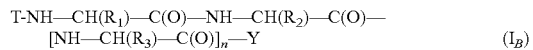

T-NH—CH($R_1$)—C(O)—NH—CH($R_2$)—C(O)— [NH—CH($R_3$)—C(O)]$_n$—Y      ($I_B$)

as defined above and in which $R_1$, $R_2$ and $R_3$ represent, independently, an alkyl radical optionally substituted by one or more substituents chosen from: hydroxy, mercapto, lower alkylthio, carboxy, aminocarbonyl, amino, guanidino, or optionally substituted phenyl, indole or imidazole,
the substituent or substituents of the phenyl, indole and imidazole radicals being chosen from: halo, hydroxy, lower alkyl or lower alkoxy;

Y represents the hydrogen atom or a —C(O)-Ry or —C(O)—O—R'y radical in which

Ry represents a lower alkyl or —N(Ry$_1$)(Ry$_2$) radical;

R'y represents a lower alkyl or benzyl radical;

Ry$_1$ represents the hydrogen atom and Ry$_2$ represents, independently, the hydrogen atom, a lower alkyl, lower alkoxy, lower arylalkyl, lower heteroarylalkyl, cycloalkyl-alkyl, heterocycloalkyl radical, these radicals being able to be substituted by one or more identical or different substituents chosen from: halo, hydroxy, trifluoromethyl, lower alkyl, lower alkoxy, amino, (lower alkyl)amino, di(lower alkyl)amino, aryloxy, arylalkoxy;

n represents 0 or 1;

T represents a radical of formula —C(O)—O-Rt$_1$ or —C(O)-Rt$_2$ in which

Rt$_1$ represents a lower alkyl, benzyl, phenethyl radical;

Rt$_2$ represents a lower alkyl, lower arylalkyl, lower aryloxy alkyl or a heteroaryl radical.

Quite preferentially, a subject of the invention is a composition or a product as defined above, characterized in that the calpain inhibitor corresponds to formula ($I_B$)

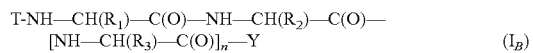

T-NH—CH($R_1$)—C(O)—NH—CH($R_2$)—C(O)— [NH—CH($R_3$)—C(O)]$_n$—Y      ($I_B$)

as defined above and in which $R_1$ and $R_2$ represent, independently, an alkyl radical optionally substituted by a phenyl radical, itself optionally substituted by halo, hydroxy;

Y represents the-hydrogen atom;

T represents a radical of formula —C(O)—O—Rt, in which Rt$_1$ represents a lower alkyl or benzyl radical, and n=0.

A more particular subject of the invention is also a composition or a product as defined above, characterized in that the reactive oxygen species trap is chosen from ascorbic acid, ethoxyquin, N-acetyl-cysteine, β-carotene, 2,2,5,5-tetramethyl-3-pyrroline-1-oxyl-3-carboxylic acid, the Q10 coenzyme, captodative compounds, nitrones, phenolic compounds, indole derivatives, indolines, imidazoles, phenothiazines, phenoxazines, phenazines, diphenylamines or carbazoles.

Preferentially, a subject of the invention is a composition or a product as defined above, in which the reactive oxygen species trap is chosen from ascorbic acid, ethoxyquin, tempol, N-tert-butyl-α-phenyl-nitrone, N-acetyl-cysteine, β-carotene, 2,2,5,5-tetramethyl-3-pyrroline-1-oxyl-3-carboxylic acid, the Q10 coenzyme, captodative compounds, probucol, NDGA, α-, β-, γ-, ε-, τ- or δ-tocopherol, 3,5-ditert-butyl-4-hydroxybenzoic acid, 2,3,6-trimethyl-2-hexyloxyphenol, 2,6-di-tert-butyl4-methoxyphenol, 2,6-di-tert-butyl4-methylphenol, trolox, n-propyl gallate, eugenol, cafeic acid, sinapinic acid, gallic acid, propofol, melatonin, 5-hydroxy-tryptamine, 5-hydroxy-indole-2-carboxylic acid, 5-amino-indoline, N-methyl-indoline, imidazole, cimetidine, 4-hydroxy-carbazole, carvedilol, 2-methoxy-10H-phenothiazine, 4-hydroxydiphenylamine, 4-aminodiphenylaamine, 4-methoxy-N-(4-methoxyphenyl)aniline or 9-[2-(4-morpholinyl)ethyl]-2,4-di-1-pyrrolidinyl-9H-pyrimido [4,5-b]indole.

A more particular subject of the invention is a composition or a product as defined above, characterized in that the reactive oxygen species trap is chosen from phenolic compounds, phenothiazines and diphenylamines. Preferably, the reactive oxygen species trap is chosen from the phenolic compounds of formula $I_A$ as defined above, the phenothiazines of formula $IV_A$ as defined above and the diphenylamines of formula $V_A$ as defined above.

Also more particularly, a subject of the invention is a composition or a product as defined above and in which:
the reactive oxygen species trap is chosen from: 3,5-ditert-butyl-4-hydroxybenzoic acid (BHT), 2-methoxy-10H-phenothiazine and 4-hydroxydiphenylamine; and
the compound which inhibits calpains is chosen from: benzyl (1S)-1-({[(1S)-1-formyl-3-methylbutyl] amino}carbonyl)-3-methylbutycarbamate (or Z-Leu-Leu-H), benzyl (1S)-1-{[(1-benzyl-2-oxoethyl)amino] carbonyl}-3-methylbutylcarbamate (or Z-Leu-Phe-H), the benzyl ester of [1-[[1-formylpentyl)amino]carbonyl]-3-methylbutyl]carbamic acid (calpeptin) and 3-(4-iodophenyl)-2-mercapto-2-propenoic acid (PD 150606).

Finally, a subject of the invention is the use of a substance which inhibits calpains and a substance which traps reactive oxygen species, for the preparation of a medicament intended to treat disorders of the central or peripheral nervous system, muscular dystrophies, cachexia, loss of hearing and cataracts. Preferably, the substance which inhibits calpains is 3-(4-iodophenyl)-2-mercapto-2-propenoic acid (PD 150606) or corresponds to formula $I_B$ as defined above. Also preferably, the reactive oxygen species trap is chosen from the phenolic compounds, phenothiazines and diphenylamines, and more particularly the reactive oxygen species trap is chosen from the phenolic compounds of formula $I_A$ as defined above, the phenothiazines of formula $IV_A$ as defined above and the diphenylamiries of formula $V_A$ as defined above.

The compounds which inhibit calpains and reactive oxygen species traps are commercial or can be prepared by the methods known to a person skilled in the art (or by analogy to the latter) (J. Med. Chem., vol. 37, 2918–2929 (1994); TIPS, vol. 11, 139–142 (1990); TEBS, vol. 16, 150–153 (1991); Br. J. Pharmacol., vol. 10, 369–377 (1993)).

All the technical and scientific terms used in the present text have the meaning known to a person skilled in the art. Moreover, all the patents (or patent applications) as well as the other bibliographical references are incorporated by way of reference.

Experimental Part

The following examples are presented in order to illustrate the above procedures and should in no case be considered as a limit to the scope of the invention.

Let A be the reactive oxygen species trap and B the calpain inhibitor

EXAMPLE 1

Compound AB, combination of compound A: 3-5-di-tert-butyl4-hydroxybenzoic acid (BHT), an antioxidant which traps free oxygen radicals, and compound B: Z-Leu-Leu-H, a calpain inhibitor.

EXAMPLE 2

Compound AB, a combination of compound A: 2-methoxy-10H-phenothiazine, an antioxidant which traps free oxygen radicals, and compound B: Z-Leu-Phe-H, a calpain inhibitor.

EXAMPLE 3

Compound AB, a combination of compound A: 3-5-di-tert-butyl-4-hydroxybenzoic acid (BHT), an antioxidant which traps free oxygen radicals, and compound B: calpeptin, a calpain inhibitor.

EXAMPLE 4

Compound AB, a combination of compound A: 3,5-di-tert-butyl-4-hydroxybenzoic acid (BHT), an antioxidant which traps free oxygen radicals, and compound B: 3-(4-iodophenyl)-2-mercapto-2-propenoic acid (PD 150606), a calpain inhibitor.

EXAMPLE 5

Compound AB, a combination of compound A: 4-hydroxydiphenylainine, an antioxidant which traps free oxygen radicals, and compound B: 3-(4-iodophenyl)-2-mercapto-2-propenoic acid (PD 150606), a calpain inhibitor.

EXAMPLE 6

Compound AB, a combination of compound A: 4-hydroxydiphenylamine, an antioxidant which traps free oxygen radicals, and compound B: Z-Leu-Leu-H, a calpain inhibitor.

EXAMPLE 7

Compound AB, a combination of compound A: 2-methoxy-10H-phenothiazine, an antioxidant which traps free oxygen radicals, and compound B: calpeptin, a calpain inhibitor.

Pharmacological Study

The compounds of the invention were subjected to some biological tests in vitro, in order to prove their activity in blocking calpain and trapping free radicals. Their activity was evaluated on enzymatic tests and on a model of protection from cell death. In this model, cell death by necrosis is induced by maitotoxin (J Neurochem 1999, 72 (5): 1853–1863, Mc Ginnis et al). Maitotoxin is a marine toxin which activates the calcium channels (Biochem. Pharmacol 1990.39:1633–1639, Gusovsky et al). There results a 10–20 fold increase in intracellular calcium in rat glial cells C6 (Chem Res Toxicol 1999:12:993-1001, Konoki et al). The treatment of SHSY5Y human neuroblastomas with maitotoxin induces activation of the calpain's activity via an increase in intracellular calcium (Archives of Biochemistry and Biophysics, 331 (2): 208–214, Wang et al). The calpains are cytosolic protease cysteines which absolutely require calcium in order to be activated. Two isoforms of calpain are distributed ubiquitously in the tissues: calpain I or "µ" and calpain II or "m" which respectively require a FM or mM concentration of calcium in order to be activated.

In the in situ model of necrosis induced by maitotoxin, stimulation of the calpain and production of reactive oxygen species occur. The partial protective effect on the necrosis of a calpain inhibitor or reactive oxygen species trap is demonstrated. The effects of the association were compared with those produced by treatment with the calpain inhibitor or reactive oxygen species trap alone. The association of a calpain inhibitor and an reactive oxygen species trap shows a significant protective effect on the necrosis induced by maitotoxin compared to the effect of the calpain inhibitor or reactive oxygen species trap taken separately and at the doses used. This proves the synergy between the calpain inhibitor and the reactive oxygen species trap.

1) Study of the Effects on Human Calpain I

The test consists of measuring the activity of the enzyme (enzyme purified from human erythrocytes) which is incubated in a buffer in the presence of a peptide substrate coupled with a fluorochrome (amino-methylcourmarin, AMC) and calcium. The enzyme activated by the calcium, proteolyses the substrate and releases the AMC fragment. The AMC released fluoresces at 460 nm under excitation at 380 nm. The activity of the enzyme is therefore proportional to the quantity of fluorescence i.e. of free AMC fragment. The fluorescence (380/460 nm) is measured using a multi-well fluorimeter (Victor 2, Wallac).

Assay is carried out in 96-well microplates with transparent bottoms and black walls in which 10 µl per well of substance to be tested in DMSO 10%, 45 µl of reaction mixture containing the human calpain I at 2.2 U/ml (Calbiochem, ref: 208713), the Suc Leu Tyr-AMC substrate (Bachem, ref: I-1355) at 1.1 mM in a buffer (Tris-HCl 110 mM; NaCl 110 mM; EDTA 2.2 mM; EGTA 2.2 mM; mercaptoethanol 1.1 mM) are distributed. The reaction is initiated by adding 45 µl of $CaCl_2$ 22 mM. To determine the background noise, control wells without calcium are added to the plate (10 µL DMSO 10%+45 PL of buffer with the enzyme and the susbtrate +45 µL $H_2O$). In order to determine the total activity of the enzyme control wells containing no product are added to the plate (10 µL DMSO 10%+45

μL of buffer with the enzyme and the substrate +45 ItL of CaCl$_2$ 22 mM). Each concentration of the products (0.1 nM to 10 μM) is tested in duplicate. The plates are shaken and incubation takes place for one hour at 25° C. in darkness. The fluorescence is read at 380/460 nm using the Victor.

The results are expressed as IC$_{50}$ values and are summarized in Table 1 below.

2) In Situ Effect on Calpain Activity in Human Neuroblastomas (SHSY5Y) and in Rat Glial Cells (C6)

Human neuroblastomas SHSY5Y and rat glial cells C6 are seeded at a rate of 50,000 and 25,000 cells respectively per well on 96-well plates in DMEM 10% FBS. The next day, the cells which have adhered are washed 3 times in DMEM medium without serum and 40 mM Hepes. 100 microlitres of product B is placed in the wells. After incubation for 1 hour at 37° C. under an atmosphere of 5% CO$_2$, 10 μl containing the fluorescent substrate of calpain (Suc-Leu-Tyr-AMC) and maitotoxin (Sigma, ref: M-9159), in order to obtain a final concentration in the well of 100 μM and of 1 nM respectively are added.

In order to determine the total activity of the cell enzyme, wells containing no product are added to the plate (100 μL DMSO 100$^{th}$ plus 10 μl of MTX and substrate). The background noise is determined by adding control wells with no MTX. Each concentration of the products (0.3 FM to 200 μM for the SHSY5Y's and 0.01 μM to 100 μM for the C6's) is tested in triplicate. The plates are shaken, the fluorescence is read at 380/460 nm using the Victor at T zero. Incubation takes place for four hours for the SHSY5Y and 1 hour 30 minutes for the C6 cells at 30° C. in darkness.

The results are expressed as IC$_{50}$ values and summarized in Table 1 below.

TABLE 1 enzymatic inhibition activity of compounds A and B

| | Inhibition human calpain I [IC$_{50}$ (nM)] | | |
|---|---|---|---|
| | acellular | in situ (SHSY5Y) (n = 6) | in situ (C6) (n = 3) |
| LEUPEPTIN | 73 | | |
| EXAMPLE 1 | | | |
| A | — | — | — |
| B | 6 | 13370 ± 2390 | 1750 ± 340 |
| EXAMPLE 2 | | | |
| A | — | — | — |
| B | 8 | — | 2200 ± 290 |
| EXAMPLE 3 | | | |
| A | — | | |
| B | 2.8 | | |
| EXAMPLE 4 | | | |
| A | — | | |
| B | 5144 | | |
| EXAMPLE 5 | | | |
| A | — | | |
| B | 5144 | | |
| EXAMPLE 6 | | | |
| A | — | | |
| B | 6 | | |
| EXAMPLE 7 | | | |
| A | — | | |
| B | 2.8 | | |

(leupeptin as well as Examples 3 to 7 were only tested on the inhibition of acellular human calapin I).

3) In Vitro Effect on Lipidic Lipoperoxidation

The test consists of inducing lipidic peroxidation by Fenton reactions in the presence of iron and ascorbate. The degree of lipidic peroxidation is determined by the concentration of malonaldehyde (MDA). The MDA produced by the lipidic peroxidation of unsaturated fatty acids is a good indicator of lipidic peroxidation (Esterbauer et al, 1990; Meth. Enzymol. 186: 407–421). For this calorimetric test, the condensation of a molecule of MDA with two molecules of chromogenic reagent R(N-methyl-2-phenylindole) produces a stable chromophore the maximum absorbance wavelength of which is equal to 586 nM.

The membranes are prepared from the cortexes of male Sprague Dawley rats weighing 200 to 250 g. The animals are sacrificed by decapitation and the brains are immediately removed and rinsed in cold Tris HCl 20 mM pH 7.4. The cortexes, after dissection and removal of the white matter, are then ground with the Thomas potter, in Tris HCl buffer 20 mM pH 7.4 at 40 C. The homogenate obtained is centrifuged at low speed in order to eliminate the large debris (515 g for 15 minutes at 40 C). The supernatant is then distributed into polycarbonate centrifugation tubes and centrifuged at 51500 g for 25 min at 4° C. The membrane pellets are kept at –80° C.

On the day of the experiment, the frozen membranes are resuspended at a concentration of 0.5 equivalent grams of cortex per 5 ml of Tris HCl buffer 20 mM pH 7.4 and homogeneized using a combitips. In 96-well "deep-well" 1 ml polypropylene plates with a conical base, 5 μl per well of the product to be tested or of solvent is mixed with 40 μl of rat cerebral cortex homogenate by centrifugation (800 rpm). The plates are covered with a self-adhesive aluminium sheet and incubated at 37° C. for 15 minutes under agitation. The lipidic peroxidation reaction is initiated by Fenton reaction by the addition of 5 μl per well of the peroxidation mixture containing 1 mM EDTA, 4 mM ascorbic acid and 1 mM FeCl$_2$, in order to form the MDA. The plates are briefly centrifuged (800 rpm) and covered with a self-adhesive aluminium sheet. After incubation for 30 minutes at 370 C under agitation, 160 μl of a developing mixture containing 3 volumes of the chromogenic reagent R and one volume of methanol is added per well. After agitation for 10 seconds, 40 μl of 37% HCl is added per well. Development of the MDA which has formed is obtained after incubation of the membranes for 45 minutes at 45° C.

The membranes and the supernatants are separated by filtration under vacuum on a 96-well plate with a multiscreen filtering base NA (Millipore, ref: MANANLY 50). The absorbance of the supernatants recovered in the 96-well plates is read using a photometer.

The results are expressed as IC$_{50}$ values and are summarized in Table 2 below.

4) In Situ Effect on the Isoprostane Level(8-isoPG1F2α)

8-isoPG1F2α is part of a family of compounds the first synthesis stage of which (peroxidation of arachidonic acid) is carried out in a non-enzymatic manner in the presence of free radicals (Morrow and coil, 1990). Measurement of the 8-iso PGF2α level is considered as a reliable marker of the oxidation stress.

The rat glial cells C6 were seeded at 25 000 cells per well in 96-well plates in DMEM 10% FBS. The next day, 100 μl of product A was placed in the wells. After incubation for 1 hour at 37° C. under an atmosphere of 5% CO$_2$, 10 μl containing maitotoxin is added in order to obtain a final concentration in the well of 1 nM. After incubation for 3 hours, the supernatants are removed and frozen at –20° C.

The 8-isoPG1F2α level is measured using a specific EIA dosage kit (Cayman chemical, ref: 516351).

The results are expressed as $IC_{50}$ (EM) values and are summarized in Table 2 below.

TABLE 2 activity on enzymatic inhibition of compounds A and B

|  | Inhibition of lipidic peroxidation [$IC_{50}$ (µM)] | Inhibition of the isoprostane count in situ (C6) [$IC_{50}$ (µM)] (n = 3) |
|---|---|---|
| EXAMPLE 1 |  |  |
| A | 3.7 | 101 |
| B | — | — |
| EXAMPLE 2 |  |  |
| A | 0.19 | 0.4 |
| B | — | — |
| EXAMPLE 3 |  |  |
| A | 3.7 |  |
| B | — |  |
| EXAMPLE 4 |  |  |
| A | 3.7 |  |
| B | — |  |
| EXAMPLE 5 |  |  |
| A | 0.093 |  |
| B | — |  |
| EXAMPLE 6 |  |  |
| A | 0.093 |  |
| B | — |  |
| EXAMPLE 7 |  |  |
| A | 0.19 |  |
| B | — |  |

(leupeptin as well as Examples 3 to 7 were only tested on the inhibition of acellular human calapin I).

5) In Vitro Effect on Necrosis Induced by Maitotoxin

Human neuroblastomas SHSY5Y and rat glial cells C6 are seeded at 25 000 cells per well in 96-well plates in DMEM 10% FBS for 24 hours. The L6 rat myoblasts are seeded at 1000 cells per well in DMEM 10% FBS on 96-well microplates coated beforehand with gelatin 0.5% PBS. After culture for 3 days the medium is removed and replaced with a differentiation medium (DMEM+10 µg/ml of insulin +100 µg/ml of transferrin). 50 µl of product A plus 50 µl of solvent or 50 µl of product B are placed in the wells. After incubation for 1 hour at 370 C under an atmosphere of 5% $CO_2$, 10 µl of maitotoxin is added in order to obtain a final concentration of 0.1 nM to 1 mM (according to the cell type). After incubation for 3 hours at 37° C. under an atmosphere of 5% $CO_2$, the cell viability is determined by adding 10 µl of tetrazolium salts (wst-1, Roche, ref: 1644807). The tetrazolium salts are cleaved into formazan molecules by mitochondrial dehydrogenases. The quantity of formazan formed is directly correlated to the number of metabolically active cells in the culture. Measurement of the absorbance of the formazan is carried out using a multiwell photometer at a wavelength of 420 nm against a reference wavelength of 620 nm. The results are expressed as a percentage protection against necrosis induced by 0.1 nM maitotoxin and are summarized in Tables 4 and 5 below.

The theoretical effect was obtained by multiplying the percentage of dead cells in the presence of product A by the percentage of dead cells in the presence of product B (Table 3). The percentage protection against cell death induced by MTX being the percentage of cells kept alive in the presence of the product or products.

TABLE 3

Determination of the interaction of compounds A and B.

| Dead Fraction obtained after combining compounds A and B Effect observed | Dead Fraction obtained by each of compounds A and B Theoretical effect | Interaction of compounds A and B |
|---|---|---|
| DF (A + B) < | (DF A) × (DF B) | synergy |
| DF (A + B) = | (DF A) × (DF B) | additivity |
| DF (A + B) > | (DF A) × (DF B) | antagonist |

In a first series of experiments, the concentration of product A in Example 1 is fixed (100 µM), product B is added at concentrations varying from zero to 100 µM (Table 4A). In a second series of experiments, product B of Example 1 is fixed at 100 µM, product A is added at concentrations varying from zero to 100 µM (Table 4B). It is the association with 100 µM of each of the products which shows the greatest synergy between product A and product B to protect the SHSY5Y cells from necrosis induced by MTX.

TABLE 4

Protection from necrosis induced by 0.1 nM maitotoxin on human neuroblastomas SHSY5Y (n = 2)

Table 4A: Interaction of compound A (BHT) (concentration fixed at 100 µM) in the presence of varying concentrations of compound B (Z-Leu-Leu-H).

|  | Protection from necrosis induced by MTX | | | | |
|---|---|---|---|---|---|
|  | A | B | | | |
|  | 100 µM | 12.5 µM | 25 µM | 50 µM | 100 µM |
| compound A (100 µM) | 8.68 ± 0.3 |  |  |  |  |
| compound B |  | 6.89 ± 1.51 | 6.94 ± 0.2 | 9.01 ± 0.83 | 17.52 ± 2.69 |
| compound A + compound B Effect observed |  | 24.90 ± 0.93 | 32 ± 0.93 | 35.74 ± 5.71 | 44.07 ± 16.62 |
| compound A + compound B Theoretical effect |  | 14.98 ± 1.1 | 15.01 ± 0.46 | 16.91 ± 1.03 | 24.68 ± 2.2 |

TABLE 4-continued

Protection from necrosis induced by 0.1 nM maitotoxin on human neuroblastomas SHSY5Y (n = 2)

Table 4B: Interaction of compound B (Z-Leu-Leu-H) fixed (100 μM) in the presence of varying concentrations of compound A (BHT)

| | Protection from necrosis induced by MTX | | | | |
|---|---|---|---|---|---|
| | B | A | | | |
| | 100 μM | 12.5 μM | 25 μM | 50 μM | 100 μM |
| compound B (100 μM) | 17.52 ± 2.69 | | | | |
| compound A | | 5.18 ± 1.81 | 7.45 ± 1.65 | 8.87 ± 0.34 | 8.68 ± 0.3 |
| compound A + compound B Effect observed | | 22.08 ± 4.49 | 27.38 ± 2.46 | 30.71 ± 11.01 | 44.07 ± 16.62 |
| compound A + compound B Theoretical effect | | 21.38 ± 1.06 | 23.7 ± 1.13 | 24.82 ± 2.73 | 24.68 ± 2.2 |

In the light of the previous results, the combination of Example 1 with product A and product B at a rate of 100 μM of each of the products is carried out on human neuroblastomas (SHSY5Y; (Table 5A) and on glial cells with 25 μM of product A and 50 μM of product B (C6; Table 5B) on a larger number of cases.

TABLE 5

Synergistic interaction of compounds A and B on protection from necrosis.
TABLE 5A:

| Products at 100 μM | Protection from necrosis induced by MTX on SHSY5Y (n = 8) |
|---|---|
| EXAMPLE 1 | |
| A | 19.48 ± 5.20% |
| B | 12.87 ± 3.72% |
| AB observed | 40.35 ± 6.21% */A, **/B, greater than theoretical |
| NB theoretical | 28.69 ± 6.73% |

The results of Table 5A, Example 1 show that the Z-Leu-Leu-H calpain inhibitor, used at a concentration of 100 μM, is not active to effectively protect human neuroblastomas (SHSY5Y) from necrosis induced by maitotoxin. Similarly, 3,5-di-tert-butyl4-hydroxybenzoic acid used as a reactive oxygen species trap at a dose of 100 μM is weakly active (less than 20%). On the other hand, the association of the two compounds offers significant protection compared with the two compounds tested separately. This effect is synergistic, as the percentage protection obtained by combining the two compounds is greater than the calculated theoretical effect (Tables 3 and 5A, Example 1).

TABLE 5B

| Products | Protection from necrosis induced by MTX on C6[a] |
|---|---|
| EXAMPLE 1 | 9.69% |
| B [50 μM] | 21.23% |
| A [25 μM] | 43.95% |
| A [50 μM] B [25 μM] observed | 28.59% |
| AB theoretical | |
| EXAMPLE 2 | |
| A [50 μM] | 6.56 ± 1.6% |
| B [50 μM] | 12.05 ± 2.82% |

TABLE 5B-continued

| Products | Protection from necrosis induced by MTX on C6[a] |
|---|---|
| A [50 μM] B [50 μM] observed | 33.06 ± 7.99% |
| AB theoretical | 17.77 ± 3.68% |
| EXAMPLE 3 | |
| B [100 μM] | 0.84% |
| A [50 μM] | 12.51% |
| A [100 μM] B [50 μM] observed | 37.77% |
| AB theoretical | 13.25% |
| EXAMPLE 4 | |
| B [100 μM] | 0.36% |
| A [100 μM] | 30.84% |
| A [100 μM] B [100 μM] observed | 60.90% |
| AB theoretical | 31.09% |
| B [100 μM] | 2.75% |
| A [25 μM] | 16.17% |
| A [25 μM] B [100 μM] observed | 27.15% |
| AB theoretical | 18.47% |
| EXAMPLE 5 | |
| B [25 μM] | 0.69% |
| A [100 μM] | 17.90% |
| A [25 μM] B [100 μM] observed | 29.73% |
| AB theoretical | 18.47% |
| EXAMPLE 6 | |
| B [50 μM] | 4.91% |
| A [100 μM] | 9.43% |
| A [50 μM] B [100 μM] observed | 31.21% |
| AB theoretical | 13.88% |
| EXAMPLE 7 | |
| B [50 μM] | 13.03% |
| A [100 μM] | 10.45% |
| A [50 μM] B [100 μM] observed | 62.09% |
| AB theoretical | 22.12% |

[a] n = 1 for Examples 1 and 3 to 7 and n = 3 for Example 2

As with Table 5A, the results of Table 5B, Example 1 show that the Z-Leu-Leu-H calpain 5 inhibitor, used a concentration of 50 μM, is not active to effectively protect rat glial cells (C6) from necrosis induced by maitotoxin. Similarly, 3–5-di-tert-butyl-4-hydroxybenzoic acid used as a reactive oxygen species trap at a dose of 25 μM is weakly active (of the order of 20%). On the other hand, the association of the two compounds offers protection compared with the two compounds tested separately (43%). This effect is synergistic, as the percentage protection obtained by association of the two compounds is greater than the calculated theoretical effect (Tables 3 and 5B, Example 1).

The synergistic effect of an anti-ROS and an anti-calpain on the protection from necrosis induced by MTX was verified on glial cells with another antioxidant and another calpain inhibitor (Example 2, Table 5B).

Similarly, 2-methoxy-10H-phenothiazine, an antioxidant which traps reactive oxygen species, and Z-Leu-Phe-H, a calpain inhibitor, are inactive at a dose of 50 µM in protecting the rat glial cells (C6) from necrosis induced by maitotoxin. On the other hand, the association of 2-methoxy-10H-phenothiazine with Z-Leu-Phe-H (Table 5, Example 2) shows highly significant protection compared with the two compounds tested separately as well as the theoretical association. This effect is significantly synergistic, as the percentage protection obtained by association of the two compounds is significantly greater than the calculated theoretical effect (Tables 3 and 5B).

The synergistic effect of other antioxidants and other calpain inhibitors was also tested on glial cells (Examples 3 to 7; Table 5B). Example 7 was reproduced on another cell line in particular rat skeletal muscle cells (myoblasts differentiated to myotubes; Table 5C). In these examples, products A and B offer little protection vis a vis cell necrosis induced by—maitotoxin, on the other hand, the combination of the two compounds offers protection compared with the two compounds tested separately. These effects are synergistic, as the percentage protection obtained by association of the two compounds is greater than the calculated theoretical effect (Tables 3, 5B, Example 3 to 7 and 5C Example 7).

TABLE 5C

| Products | Protection from necrosis induced by MTX on L6 Myoblasts differentiated to myotubes (rat skeletal muscle cells) |
|---|---|
| EXAMPLE 7 | |
| B[100 µM] | 5.09% |
| A[100 µM] | 10.94% |
| A [100 µM] B [100 µM] observed | 25.05% |
| AB theoretical | 15.48% |

The invention claimed is:

1. A pharmaceutical composition comprising, as active ingredient, a synergistic mixture of at least one calpain inhibitor substance and at least one reactive oxygen species trapping substance, and optionally a pharmaceutically acceptable support, wherein the reactive oxygen species trap is selected from the group consisting of 3,5-di-tert-butyl-4-hydroxybenzoic acid (BHT), 2-methoxy-10H-phenothiazine and 4-hydroxydiphenylamine; and the compound which inhibits calpains is selected from the group consisting of benzyl (1S) -1-({[(1S)-1-formyl-3-methylbutyl]amino}carbonyl)-3-methylbutylcarbamate, benzyl (1S)-1-{[(1-benzyl-2-oxoethyl)amino]carbonyl}-3-methylbutylcarbamate, the benzyl ester of [1[[1-formylpentyl)aminocarbonyl]-3-methylbutyl]carbamic acid (calpeptin) and 3-(4-iodophenyl)-2-mercapto-2-propenoic acid.

* * * * *